US00PP32305P3

(12) United States Plant Patent
Pakozdi et al.

(10) Patent No.: US PP32,305 P3
(45) Date of Patent: Oct. 13, 2020

(54) STRAWBERRY PLANT NAMED 'DRISSTRAWSEVENTYTHREE'

(50) Latin Name: ***Fragaria* x *ananassa***
Varietal Denomination: DrisStrawSeventyThree

(71) Applicant: Driscoll's, Inc., Watsonville, CA (US)

(72) Inventors: Katalin Monika Pakozdi, Maidstone (GB); Katarzyna Blake, Watsonville, CA (US); Maria Cruz Ayuso Hernandez, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,198

(22) Filed: Mar. 5, 2019

(65) Prior Publication Data

US 2020/0288615 P1 Sep. 10, 2020

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./208, 209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
(Continued)

OTHER PUBLICATIONS

"An Early Season with Many highs", Berry Gardens, Available Online at <https://www.berrygardens.co.uk/an-early-season-with-many-highs/>, Aug. 21, 2017, 6 pages.
Fear et al., Unpublished U.S. Appl. No. 15/998,014, filed Jun. 11, 2018; titled "Strawberry Plant Variety Named 'DrisStrawFiftyEight'".
Ferguson et al. Unpublished U.S. Appl. No. 15/998,317, filed Aug. 3, 2018, titled "Strawberry Plant Variety Named 'DrisStrawSixty'".
Katie, "My Green Pod", Available online at <https://www.mygreenpod.com/articles/its-strawberry-time/>, May 30, 2017, 3 pages.
(Continued)

*Primary Examiner* — Susan McCormick Ewoldt
(74) *Attorney, Agent, or Firm* — Morrison & Foerster LLP

(57) ABSTRACT

A new and distinct variety of strawberry plant named 'DrisStrawSeventyThree', selected for its conical fruit shape, juicy fruit flesh with good post-harvest qualities, large fruit size, healthy and strong plants, and productivity, is disclosed.

3 Drawing Sheets

(56) References Cited

U.S. PATENT DOCUMENTS

| | | | |
|---|---|---|---|
| PP20,248 | P3 | 9/2009 | Rogers et al. |
| PP20,363 | P2 | 9/2009 | Chandler |
| PP20,701 | P2 | 2/2010 | Gilford et al. |
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| 2003/0079263 | P1 | 4/2003 | Gilford et al. |
| 2013/0276182 | P1 | 10/2013 | Fear et al. |

OTHER PUBLICATIONS

Mendoza et al., Unpublished U.S. Appl. No, 16/350,139, filed Oct. 2, 2018, titled "Strawberry Plant Variety Named 'Dris-StrawSixtySeven'".

Mendoza et al., Unpublished U.S. Appl. No. 15/998,020, filed Jun. 12, 2018, titled "Strawberry Plant Variety Named 'Dris-StrawSixtyOne'".

Mendoza et al., Unpublished U.S. Appl. No. 15/998,169, filed Jul. 12, 2018, titled "Strawberry Plant Variety Named 'Dris-StrawSixtyThree'".

Mendoza et al., Unpublished U.S. Appl. No. 15/998,170, filed Jul. 12, 2018, titled "Strawberry Plant Variety Named 'Dris-StrawSixtyTwo'".

Pakozdi et al., Unpublished U.S. Appl. No. 15/998,015, filed Jun. 11, 2018, titled "Strawberry Plant Variety Named 'Dris-StrawFiftyNine'".

Pakozdi et al., Unpublished U.S. Appl. No. 15/998,028, filed Jun. 14, 2018, titled "Strawberry Plant Variety Named 'Dris-StrawSixtyFive'".

Pakozdi et al., Unpublished U.S. Appl. No. 16/501,200, filed Mar. 5, 2019, titled "Strawberry Plant Variety Named 'Dris-StrawSeventyTwo'".

Pakozdi et al., Unpublished U.S. Appl. No. 16/501,182, filed Mar. 5, 2019, titled "Strawberry Plant Variety Names 'Dris-StrawSeventyFour'".

Stewart et al., Unpublished U.S. Appl. No. 15/998,031, filed Jun. 14, 2018, titled "Strawberry Plant Variety Named 'DrisStrawSixtyFour'".

Stewart et al., Unpublished U.S. Appl. No. 16/350,432, filed Nov. 14, 2018, titled "Strawberry Plant Variety Named 'Dris-StrawSixtySix'".

STRAWBERRY PLANT NAMED 'DRISSTRAWSEVENTYTHREE'

Latin name: Botanical classification: *Fragaria* x *ananassa.*

Varietal denomination: The varietal denomination of the claimed variety of strawberry plant is 'DrisStrawSeventyThree'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSeventyThree'.

Strawberry plant variety 'DrisStrawSeventyThree' was discovered in Huelva, Spain in 2014, and originated from a cross between the female parent 'DrisStrawThirtyFour' (U.S. Pat. No. 24,395) and the male parent 'VES 030-092' (unpatented). 'DrisStrawSeventyThree' was first asexually propagated via stolons in Valladolid, Spain in 2014.

'DrisStrawSeventyThree' was subsequently asexually propagated via stolons and underwent further testing in Huelva, Spain for three years (from 2015 to 2018). The present variety has been found to be stable and reproduce true to type through successive asexual propagations via stolons.

'DrisStrawSeventyThree' exhibits the following distinguishing characteristics when grown under normal horticultural practices in Huelva, Spain:

1. Horizontal attitude of hairs on pedicels;
2. Absent or very narrow width of band without achenes on fruit
3. Achenes level with surface of fruit; and
4. Calyx attachment inserted in fruit.

'DrisStrawSeventyThree' was selected for its conical fruit shape, juicy fruit flesh with good post-harvest qualities, large fruit size, healthy and strong plants, and productivity.

DESCRIPTION OF THE DRAWINGS

This new strawberry plant is illustrated by the accompanying photographs. The colors shown are as true as can be reasonably obtained by conventional photographic procedures. The photographs are of plants that are five months from planting.

DESCRIPTION OF THE NEW VARIETY

Figure 1:
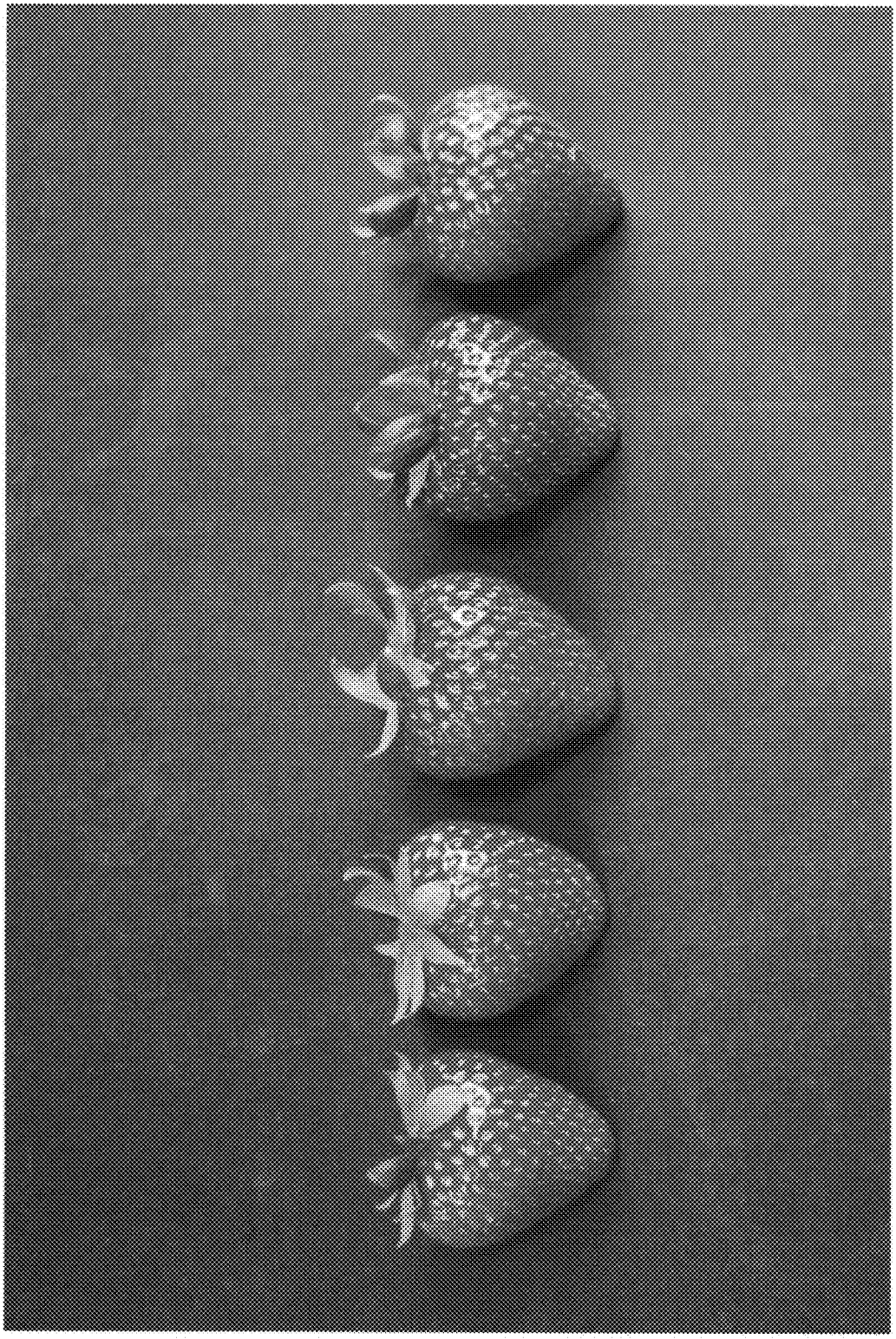
FIG. 1 illustrates whole fruit of variety 'DrisStrawSeventyThree'.
Figure 2:
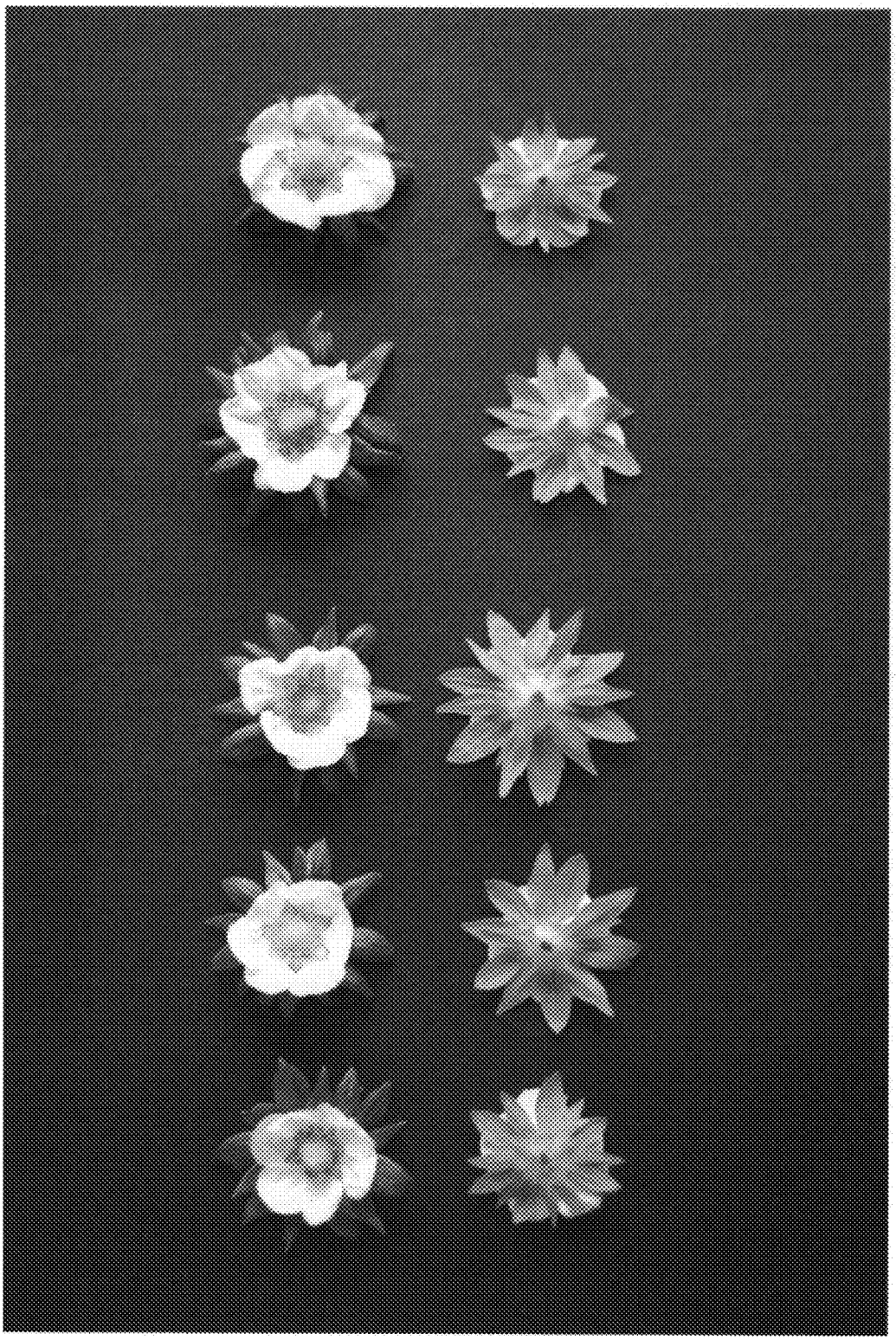
FIG. 2 illustrates the upper and lower surfaces of flowers of variety 'DrisStrawSeventyThree'.
Figure 3:
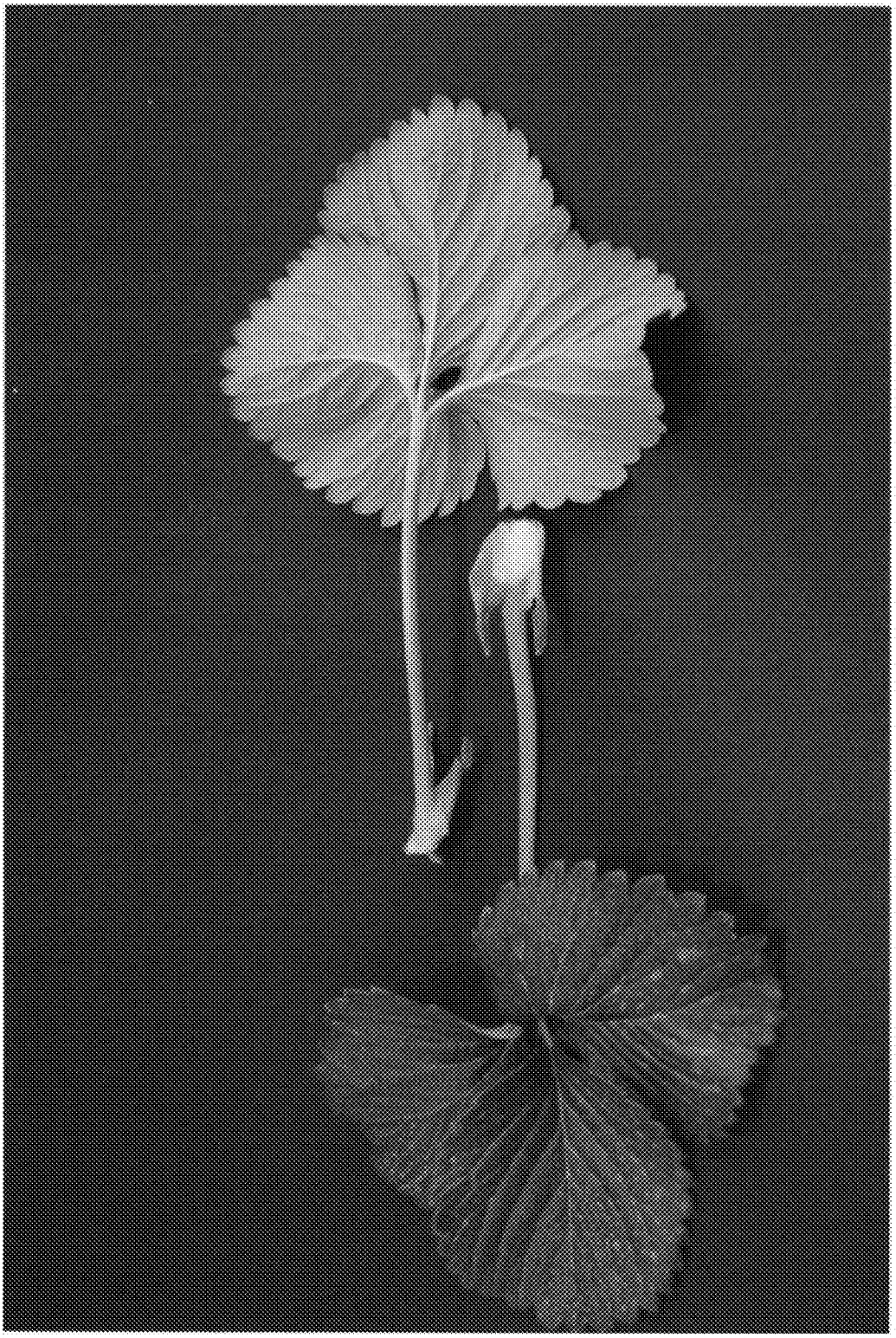
FIG. 3 illustrates the upper and lower surfaces of leaves of variety 'DrisStrawSeventyThree'.

The following detailed descriptions set forth the distinctive characteristics of 'DrisStrawSeventyThree'. The data which define these characteristics is based on observations taken in Huelva, Spain from 2015 to 2018. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSeventyThree' has not been observed under all possible environmental conditions. The botanical description of 'DrisStrawSeventyThree' was taken from plants that were five months from planting. The indicated values represent averages calculated from measurements of several plants. Color references are primarily to The RHS Colour Chart of The Royal Horticultural Society of London (RHS) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria* x *ananassa.*

*Common name.*—Strawberry.

*Denomination.*—'DrisStrawSeventyThree'.

Parentage:

*Female parent.*—Strawberry variety 'DrisStrawThirtyFour' (U.S. Pat. No. 24,395).

*Male parent.*—Strawberry variety 'VES 030-092' (unpatented).

Plant:

*Height.*—26.7 cm.

*Diameter.*—41 cm.

*Number of crowns per plant.*—3.

*Growth habit.*—Semi-upright.

Stolon:

*Average number of daughter plants per square foot.*—4.

*Diameter at bract.*—3.88 mm.

*Anthocyanin coloration.*—Present.

*Stolon color with anthocyanin coloration present.*—RHS 180B (Moderate red).

*Length.*—40 cm.

Leaf:

*Number of leaflets.*—Three only.

*Color of upper surface.*—RHS 147A (Moderate olive green).

*Color of lower surface.*—RHS N138C (Pale green).

*Venation Pattern.*—Cross-venulate.

*Leaf size (excluding petiole and stipules).*—Medium.

*Variegation.*—Absent.

*Terminal leaflets.*—Length: 7.47 cm. Width: 7.68 cm. Length/width ratio: 0.97. Number of teeth/terminal leaflet: 19.1. Shape of base: Obtuse. Margin: Crenate. Shape in cross section: Concave.

*Petiole.*—Length: 12.1 cm. Diameter: 2.70 mm. Attitude of hairs: Horizontal. Bract frequency (number present on each petiole): 2. Color: RHS 144A (Strong yellow-green).

*Petiolule.*—Length: 8.7 mm. Diameter: 1.55 mm. Color: RHS 144C (Strong yellow-green).

*Stipule.*—Length: 3.4 cm. Width: 9.9 mm. Anthocyanin color: RHS 144D (Light yellow-green).

Inflorescence:

*Position in relation to foliage.*—Above.

*Peduncle.*—Length: 22.2 cm. Diameter: 3.93 mm. Color: RHS 144C (Strong yellow-green).

*Pedicel.*—Attitude of hairs: Horizontal.

*Flower bud.*—Length: 17.98 mm. Diameter: 10.43 mm. Color: RHS 143B (Strong yellow-green).

*Flower.*—Flower diameter (petal tip to petal tip on non-flattened flower): 29.9 mm. Typical and observed number of flowers per plant: 33. Arrangement of petals: Overlapping. Stamen: Present.

*Petal.*—Length: 12.8 mm. Width: 12.9 mm. Length/width ratio: 0.99. Typical and observed petal number: 6.6. Color of upper side: RHS N155C (White). Color of under side: RHS N155B (White). Shape of apex: Rounded. Shape of base: Concave to convex. Margin: Entire.

*Calyx.*—Diameter (sepal tip to sepal tip, measured on back of flower): 42.2 mm.

*Sepal.*—Length (sepal tip to point of attachment to receptacle): 16 mm. Width: 6.5 mm. Typical and observed sepal number: 12.7. Color: RHS NN137B (Greyish olive green).

Fruit:

*Length.*—45.2 mm.

*Width.*—43.3 mm.

*Length/width ratio.*—1.04.

*Fruit hollow length.*—12.7 mm.

*Fruit hollow width.*—4.3 mm.

*Fruit hollow length/width ratio.*—2.93.

*Shape.*—Conical.

*Color.*—RHS N34A (Moderate red).

*Position of achenes.*—Level with surface.

*Position of calyx attachment.*—Inserted.

*Attitude of sepals.*—Upwards.

*Color of flesh (excluding core).*—RHS 32A (Vivid reddish orange).

*Color of core.*—RHS 31C (Strong yellowish pink).

*Average weight per berry.*—33 grams.

Production:

*Flowering interval.*—Mid-November to mid-May.

*Harvest interval.*—Late December/January to mid-May.

*Type of bearing.*—Not remontant.

*Productivity.*—0.850 kg to 1 kg of fruit per plant per season from 6.5-month-old plants when grown in Huelva, Spain.

Resistance to pests and diseases:

*Strawberry aphid (Chaetosiphon fragaefolii).*—Moderately susceptible.

*Two-spotted spider mite (Tetranychus urticae).*—Moderately susceptible.

*Powdery mildew (Podosphaera macularis).*—Moderately resistant.

COMPARISON WITH PARENTAL AND COMMERCIAL VARIETIES

'DrisStrawSeventyThree' differs from the female parent 'DrisStrawThirtyFour' (U.S. Pat. No. 24,395) in that 'DrisStrawSeventyThree' has better fruit post-harvest quality and a later maturity as compared to 'DrisStrawThirtyFour'.

'DrisStrawSeventyThree' differs from the male parent 'VES 030-092' (unpatented) in that 'DrisStrawSeventyThree' has better fruit post-harvest quality and an earlier maturity as compared to 'VES 030-092'. Further, fruit of 'DrisStrawSeventyThree' are much larger in size than fruit of 'VES 030-092'.

'DrisStrawSeventyThree' differs from the commercial variety 'DrisStrawTwentySeven' (U.S. Pat No. 23,400) in that fruit of 'DrisStrawSeventyThree' have absent or very narrow width of band without achenes, whereas fruit of 'DrisStrawTwentySeven' have very broad width of band without achenes. Further, fruit of 'DrisStrawSeventyThree' have achenes level with surface, whereas fruit of 'DrisStrawTwentySeven' have achenes below surface. Moreover, fruit of 'DrisStrawSeventyThree' have calyx attachment inserted in fruit, whereas fruit of 'DrisStrawTwentySeven' have calyx attachment raised from fruit. In addition, fruit of 'DrisStrawSeventyThree' have a strong adherence of calyx, whereas fruit of 'DrisStrawTwentySeven' have a weak adherence of calyx.

'DrisStrawSeventyThree' differs from the commercial variety 'DrisStrawSixteen' (U.S. Pat. No. 22,247) in that petioles of 'DrisStrawSeventyThree' have a horizontal attitude of hairs, whereas petioles of 'DrisStrawSixteen' have an upwards attitude of hairs. Further, pedicels of 'DrisStrawSeventyThree' have a horizontal attitude of hairs, whereas pedicels of 'DrisStrawSixteen' have an upwards attitude of hairs. Moreover, fruit of 'DrisStrawSeventyThree' have calyx attachment inserted in fruit, whereas fruit of 'DrisStrawSixteen' have calyx attachment level with fruit. In addition, fruit of 'DrisStrawSeventyThree' have an upwards attitude of sepals, whereas fruit of 'DrisStrawSixteen' have an outwards attitude of sepals.

We claim:

1. A new and distinct variety of strawberry plant named 'DrisStrawSeventyThree' as shown and described herein.

* * * * *